United States Patent [19]

Wilson et al.

[11] Patent Number: 5,681,680
[45] Date of Patent: Oct. 28, 1997

[54] DIFUNCTIONAL N-(2-CYANOETHENYL) SULFONAMIDES AND TONER COMPOSITIONS CONTAINING THEM

[75] Inventors: John C. Wilson; Peter S. Alexandrovich, both of Rochester, N.Y.

[73] Assignee: Eastman Kodak Company, Rochester, N.Y.

[21] Appl. No.: 644,801

[22] Filed: May 10, 1996

Related U.S. Application Data

[60] Provisional application No. 60/004,409 Sep. 27, 1995.

[51] Int. Cl.$^6$ .................................. G03G 9/087
[52] U.S. Cl. ........................................... 430/110
[58] Field of Search ......................... 430/110, 106.6

[56] References Cited

U.S. PATENT DOCUMENTS

| | | | |
|---|---|---|---|
| 3,577,354 | 5/1971 | Kehl | 252/468 |
| 3,893,934 | 7/1975 | Braun et al. | 252/62.1 |
| 4,002,776 | 1/1977 | Braun et al. | 427/19 |
| 4,464,452 | 8/1984 | Gruber et al. | 430/110 |
| 4,480,021 | 10/1984 | Lu et al. | 430/106.6 |
| 5,188,919 | 2/1993 | Dewanckele et al. | 430/110 |
| 5,391,454 | 2/1995 | Mukudai et al. | 430/110 |
| 5,405,727 | 4/1995 | Wilson et al. | 430/110 |
| 5,523,484 | 6/1996 | Wilson et al. | 430/110 |

OTHER PUBLICATIONS

W. Schulz et al in Chem. Ber. 100, pp. 2640–2648 (1967).

*Primary Examiner*—Christopher D. Rodee
*Attorney, Agent, or Firm*—John R. Everett

[57] ABSTRACT

There is provided a compound, useful in electrostatographic processes in the toner composition along with a polymeric binder, having the general structure:

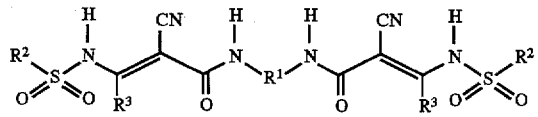

wherein $R^1$ is selected from the group consisting of alkylene; arylene; arylenedialkylene; alkylenediarylene; oxydialkylene; and substituted or unsubstituted oxydiarylene; and $R^2$ and $R^3$, which can be the same or different, are independently selected from the group consisting of alkyl containing from 1 to 20 carbons; cycloalkyl containing from 3 to 18 carbons; unsubstituted aromatic ring systems; or aromatic ring systems substituted with one or more alkyl, hydroxy, alkoxy, carboxy, carboalkoxy, nitro, halo, cyano, amino, dialkylamino, acyl, trihalomethyl or alkylsulfonyl; heteroaromatic ring systems; said ring systems having a solitary ring or 2 to 3 linked or fused rings, and containing from 3 to 34 carbons; and $R^3$ may also be ethenyl, unsubstituted or substituted with alkyl containing from 1 to 20 carbons or aryl containing from 5 to 10 carbons or aryl substituted with alkyl, hydroxy, carboxy, carboalkoxy, nitro, halo, cyano, amino, dialkylamino, acyl, trihalomethyl, or alkylsulfonyl. The described charge control agents are negative charge control agents and are essentially colorless making them particularly useful in toner compositions for color electrophotography. Thus, in another aspect of the invention, there is provided a toner composition including the charge control agent and a polymeric binder.

10 Claims, No Drawings

DIFUNCTIONAL N-(2-CYANOETHENYL) SULFONAMIDES AND TONER COMPOSITIONS CONTAINING THEM

CROSS REFERENCE TO RELATED APPLICATIONS

The present application is related to U.S. Ser. No. 08/644,805 filed on 10 May, 1996 in the names of the present inventors. That application relates to TONER COMPOSITIONS CONTAINING N-(2-CYANOETHENYL) SULFONAMIDES. In that application, the N-(2-cyanoethenyl) sulfonamides are monofunctional.

The present application is also related to U.S. Ser. No. 08/644,757 filed on even date herewith by the same inventors and entitled N-(2-CYANOETHENYL) SULFONAMIDES HAVING TWO FUNCTIONALITIES AND TONER COMPOSITIONS CONTAINING THEM. Like the present application, this related application discloses difunctional compounds but the structure of the charge control agents is different from the structure herein.

CROSS REFERENCE TO RELATED APPLICATION

Reference is made to and priority claimed from U.S. Provisional application Ser. No. 60/004,409, filed 27 Sep., 1995, entitled DIFUNCTIONAL N-(2-CYANOETHENYL) SULFONAMIDES AND TONER COMPOSITIONS CONTAINING THEM.

FIELD OF THE INVENTION

The present invention relates to electrographic materials, particularly charge control agents, and toners and developers incorporating those agents. More particularly, the invention relates to difunctional N-(2-cyanoethenyl) sulfonamide charge control agents and toners and developers including those agents.

BACKGROUND OF THE INVENTION

In electrography, image charge patterns are formed on a support and are developed by treatment with an electrographic developer containing marking particles which are attracted to the charge patterns. These particles are called toner particles or, collectively, toner. Two major types of developers, dry and liquid, are employed in the development of the charge patterns.

In electrostatography, the image charge pattern, also referred to as an electrostatic latent image, is formed on an insulative surface of an electrostatographic element by any of a variety of methods. For example, the electrostatic latent image may be formed electrophotographically, by image-wise photo-induced dissipation of the strength of portions of an electrostatic field of uniform strength previously formed on the surface of an electrophotographic element comprising a photoconductive layer and an electrically conductive substrate. Alternatively, the electrostatic latent image may be formed by direct electrical formation of an electrostatic field pattern on a surface of a dielectric material.

One well-known type of electrostatographic developer comprises a dry mixture of toner particles and carrier particles. Developers of this type are employed in cascade and magnetic brush electrostatographic development processes. The toner particles and carrier particles differ triboelectrically, such that during mixing to form the developer, the toner particles acquire a charge of one polarity and the carrier particles acquire a charge of the opposite polarity. The opposite charges cause the toner particles to cling to the carrier particles. During development, the electrostatic forces of the latent image, sometimes in combination with an additional applied field, attract the toner particles. The toner particles are pulled away from the carrier particles and become electrostatically attached, in image-wise relation, to the latent image bearing surface. The resultant toner image can then be fixed, by application of heat or other known methods, depending upon the nature of the toner image and the surface, or can be transferred to another surface and then fixed.

Toner particles often include charge control agents, which, desirably, provide high uniform net electrical charge to toner particles without reducing the adhesion of the toner to paper or other medium. Many types of positive charge control agents, materials which impart a positive charge to toner particles in a developer, have been used and are described in the published patent literature. In contrast, few negative charge control agents, materials which impart a negative charge to toner particles in a developer, are known.

Prior negative charge control agents have a variety of shortcomings. Many charge control agents are dark colored and cannot be readily used with pigmented toners, such as cyan, magenta, yellow, red, blue, and green. Some are highly toxic or produce highly toxic by products. Some are highly sensitive to environmental conditions such as humidity. Some exhibit high throw-off or adverse triboelectric properties in some uses. Use of charge control agents requires a balancing of shortcomings and desired characteristics to meet a particular situation.

Certain N-(2-cyanoethenyl)sulfonamide compounds are known in the art. The known compounds are all dicyano compounds made by a method that necessarily results in the dicyano compounds. Reference is made to Schulz, et al in Chem. Ber., 100, 2640 (1987). No use is disclosed for the three compounds made in this reference. No "difunctional" compounds, like those disclosed herein, are disclosed in this reference.

Thus, there is a continuing need for negative charge control agents which have improved properties.

SUMMARY OF THE INVENTION

The invention in its broader aspects, provides a charge control agent having the general structure:

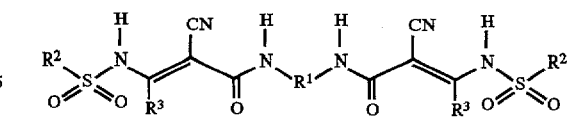

wherein $R^1$ is selected from the group consisting of alkylene; arylene; arylenedialkylene; alkylenediarylene; oxydialkylene; and substituted or unsubstituted oxydiarylene; and $R^2$ and $R^3$, which can be the same or different, are independently selected from the group consisting of alkyl containing from 1 to 20 carbons; cycloalkyl containing from 3 to 18 carbons; unsubstituted aromatic ring systems; or aromatic ring systems substituted with one or more alkyl, hydroxy, alkoxy, carboxy, carboalkoxy, nitro, halo, cyano, amino, dialkylamino, acyl, trihalomethyl or alkylsulfonyl; heteroaromatic ring systems; said ring systems having a solitary ring or 2 to 3 linked or fused rings, and containing from 3 to 34 carbons; and $R^3$ may also be ethenyl, unsubstituted or substituted with alkyl containing from 1 to 20 carbons or aryl containing from 5 to 10 carbons or aryl substituted with alkyl, hydroxy, carboxy, carboalkoxy, nitro, halo, cyano, amino, dialkylamino, acyl, trihalomethyl, or alkylsulfonyl.

Illustrative examples of alkylene include:
ethylene
1,3-propylene
1,4-butylene
1,6-hexylene
2,2-dimethyl-1,3-propylene
1,3-pentylene
2-methyl-1,5-pentylene
1,2-cyclohexylene
1,12-dodecylene
4,4'-methylenedicyclohexylene.

Illustrative examples of arylene include:
1,4-phenylene
1,3-phenylene
1,2-phenylene
2-nitro-1,4-phenylene
2,4,6-trimethyl-1,3-phenylene
2,3,5,6-tetramethyl-1,4-phenylene
4-methoxy-1,3-phenylene
2,5-dichloro-1,4-phenylene
1,5-naphthalenediyl
1,8-naphthalenediyl
1,4-anthraquinonediyl.

Illustrative examples of arylenedialkylene include:
m-xylylene
p-xylylene
o-xylylene.

Illustrative examples of alkylenediarylene include:
1,1,3-trimethyl-3-phenylindan-4',5-diyl
4,4'-methylenediphenylene.

Illustrative examples of oxydiarylene include:
4,4'-oxydiphenylene.

Illustrative examples of oxydialkylene include:
2,2'-oxydiethylene.

It is preferred that one and preferably both of $R^2$ and $R^3$ be aromatic. Thus, embodiments of the sulfonamides of the invention which are currently preferred, can be represented by the general structure:

wherein X and Y, each of which can be the same or different, are hydrogen, alkyl, hydroxy, alkoxy, carboxy, carboalkoxy, halo, nitro, cyano, amino, dialkylamino, acyl, trihalomethyl or alkylsulfonyl and $R^1$ is as defined above; and each n is independently an integer of from 0 to 5.

The above identified compounds are new compounds that are useful as charge control agents in toner compositions. Thus, in accordance with another aspect of the present invention, there is provided a toner composition comprising a polymeric binder and a charge control agent having the formula described above. Mixtures of these charge control agents can also be used.

It is an advantageous effect of at least some of the embodiments of the invention that negatively charging toners can be provided which have favorable charging characteristics and which are substantially colorless.

DESCRIPTION OF PREFERRED EMBODIMENTS

The term "particle size" as used herein, or the term "size," or "sized" as employed herein in reference to the term "particles," means the median volume weighted diameter as measured by conventional diameter measuring devices, such as a Coulter Multisizer, sold by Coulter, Inc. of Hialeah, Fla. Median volume weighted diameter is an equivalent weight spherical particle which represents the median for a sample; that is, half of the mass of the sample is composed of smaller particles, and half of the mass of the sample is composed of larger particles than the median volume weighted diameter.

The term "charge control," as used herein, refers to a propensity of a toner addendum to modify the triboelectric charging properties of the resulting toner.

The term "glass transition temperature" or "$T_g$", as used herein, means the temperature at which a polymer changes from a glassy state to a rubbery state. This temperature ($T_g$) can be measured by differential thermal analysis as disclosed in "Techniques and Methods of Polymer Evaluation," Vol. 1, Marcel Dekker, Inc., New York, 1966.

The term "melting temperature" or "$T_m$", as used herein means the temperature at which a polymer changes from a crystalline state to an amorphous state. This temperature can be measured by methods disclosed in the reference disclosed in the previous paragraph.

It is to be understood that the general structure set forth above includes geometrical isomers and tautomeric forms all of which are intended in the present invention.

The sulfonamides useful in the invention can be prepared in accordance with the following reaction scheme:

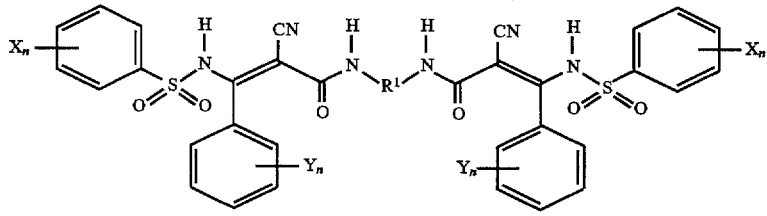

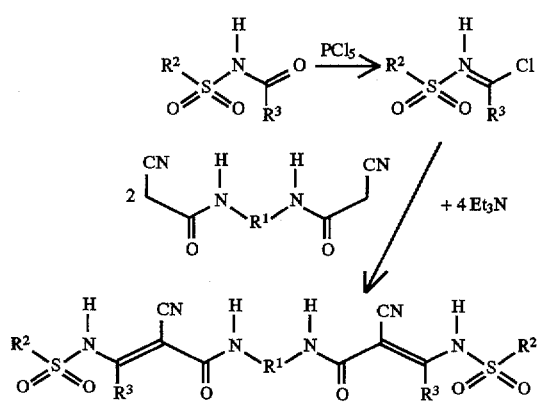

The first reaction is generally known in the art and is described for example in Barnikow and Richter, [Z, Chem., 20(3), 97(1980)]; the second reaction is known in the context of saccharin chemistry but has not been applied to compounds similar to the present invention, reference is made to Melchiorre, et at; Ann. Chim. (Rome) 1971, 61(6), 399.

The toner of the invention includes a charge control agent of the invention, in an amount effective to modify, and preferably, improve the properties of the toner. It is preferred that a charge control agent improve the charging characteristics of a toner, so the toner quickly charges to a negative value having a relatively large absolute magnitude and then maintains about the same level of charge. Relatively large values of charge per mass that are currently preferred are in the −15 to −30 microcoulombs/gram range. Exceeding the upper end of the range can result in low density on copy, and is thus not preferred. The sulfonamides of the invention are negative charge control agents, thus the toners of the invention, it is preferred, achieve and maintain negative charges having relatively large absolute magnitudes.

It is also preferred that a charge control agent improve the charge uniformity of a toner composition, that is, they insure that substantially all of the individual toner particles exhibit a triboelectric charge of the same sign with respect to a given carrier. It is also preferred that "toner throw-off" be The term "toner throw-off" refers to the amount of toner powder thrown out of a developer mix as it is mechanically agitated, for example, within a development apparatus. Throw-off can cause unwanted background development and general contamination problems. It is also preferred that a charge control agent be colorless, particularly for use in light colored toners. The charge control agents of the invention are essentially colorless. It is preferred that a charge control agent be metal free and have good thermal stability. The charge control agents of the invention are metal free and have good thermal stability. Preferred materials described herein are based upon an evaluation in terms of a combination of characteristics rather than any single characteristic.

The properties of the thermoplastic polymers employed as the toner matrix phase in the present invention can vary widely. Typically, and preferably, amorphous toner polymers having a glass transition temperature in the range of about 50° C. to about 120° C. or blends of substantially amorphous polymers with substantially crystalline polymers having a melting temperature in the range of about 65° C. to about 200° C. are utilized in the present invention. Preferably, such polymers have a molecular weight distribution including an insoluble, very high molecular weight fraction and one or more fractions having a number average molecular weight in the range of about 1000 to about 500,000 and a weight average molecular weight in the range of about $2 \times 10^3$ to about $3 \times 10^6$. Preferably, the thermoplastic polymers used in the practice of this invention are substantially amorphous. Mixtures of polymers can be employed, if desired, such as mixtures of substantially amorphous polymers with substantially crystalline polymers.

Polymers useful as binders in the toners of the invention include styrenic/acrylic copolymers. In general, preferred styrenic/acrylic copolymers have a glass transition temperature in the range of about 50° C. to about 100° C. In a particular embodiment of the invention, the resin is a copolymer of styrene and n-butyl acrylate, crosslinked with divinylbenzene produced in a suspension or emulsion polymerization process. An initiator and, optionally, a chain transfer agent are used in the synthesis. The weight ratio of styrene to n-butyl acrylate is in the range of from 90:10 to 60:40 and the divinylbenzene is used at a level of 3.0 weight percent or less, preferably, at a level of about 0.1 to 1.0 weight percent.

An optional but preferred component of the toners of the invention is colorant: a pigment or dye. Suitable dyes and pigments are disclosed, for example, in U.S. Pat. No. Re. 31,072 and in U.S. Pat. Nos. 4,160,644; 4,416,965; 4,414,152; and 2,229,513. One particularly useful colorant for toners to be used in black and white electrostatographic copying machines and printers is carbon black. Colorants are generally employed in the range of from about 1 to about 30 weight percent on a total toner powder weight basis, and preferably in the range of about 2 to about 15 weight percent.

The toners of the invention can also contain other additives of the type used in previous toners, including leveling agents, surfactants, stabilizers, and the like. The total quantity of such additives can vary. A present preference is to employ not more than about 10 weight percent of such additives on a total toner powder composition weight basis.

Dry styrenic/acrylic copolymer toners of this invention can optionally incorporate a small quantity of low surface energy material, as described in U.S. Pat. Nos. 4,517,272 and 4,758,491. Optionally the toner can contain a particulate additive on its surface such as the particulate additive disclosed in U.S. Pat. No. 5,192,637.

The charge control agent is incorporated into the toner. For example, in a dry electrostatographic toner, the charge control agent of the invention can be mixed in any convenient manner, such as blending in the manner described in U.S. Pat. Nos. 4,684,596 and 4,394,430, with an appropriate polymeric binder material and any other desired addenda. The mixture is then ground to desired particle size to form a free-flowing powder of toner particles containing the charge agent.

A preformed mechanical blend of particulate polymer particles, charge control agent, colorants and additives can, alternatively, be roll milled or extruded at a temperature sufficient to melt blend the polymer or mixture of polymers to achieve a uniformly blended composition. The resulting material, after cooling, can be ground and classified, if desired, to achieve a desired toner powder size and size distribution. For a polymer having a $T_g$ in the range of about 50° C. to about 120° C., or a $T_m$ in the range of about 65° C. to about 200° C., a melt blending temperature in the range of about 90° C. to about 240° C. is suitable using a roll mill or extruder. Melt blending times, that is, the exposure period for melt blending at elevated temperature, are in the range of about 1 to about 60 minutes. After melt blending and cooling, the composition can be stored before being ground.

Grinding can be carried out by any convenient procedure. For example, the solid composition can be crushed and then Found using, for example, a fluid energy or jet mill, such as described in U.S. Pat. No. 4,089,472. Classification can be accomplished using one or two steps.

In place of blending, the polymer can be dissolved in a solvent in which the charge control agent and other additives are also dissolved or are dispersed. The resulting solution can be spray dried to produce particulate toner powders. Limited coalescence polymer suspension procedures as disclosed in U.S. Pat. No. 4,833,060 are particularly useful for producing small sized, uniform toner particles.

The toner particles have an average diameter between about 0.1 micrometers and about 100 micrometers, and desirably have an average diameter in the range of from about 1.0 micrometer to 30 micrometers for currently used electrostatographic processes. The size of the toner particles is believed to be relatively unimportant from the standpoint of the present invention; rather the exact size and size distribution is influenced by the end use application intended. So far as is now known, the toner particles can be used in all known electrostatographic copying processes.

The amount of charge control agent used typically is in the range of about 0.2 to 7.0 weight percent. In preferred embodiments, the charge control agent is present in the range of about 0.5 to 4.0 weight percent.

The developers of the invention include carriers and toners of the invention. Carriers can be conductive, non-conductive, magnetic, or non-magnetic. Carriers are particulate and can be glass beads; crystals of inorganic salts such as aluminum potassium chloride, ammonium chloride, or sodium nitrate; granules of zirconia, silicon, or silica; particles of hard resin such as poly(methyl methacrylate); and particles of elemental metal or alloy or oxide such as iron, steel, nickel, carborundum, cobalt, oxidized iron and mixtures of such materials. Examples of carriers are disclosed in U.S. Pat. Nos. 3,850,663 and 3,970,571. Especially useful in magnetic brush development procedures are iron particles such as porous iron, particles having oxidized surfaces, steel particles, and other "hard" and "soft" ferromagnetic materials such as gamma ferric oxides or ferrites of barium, strontium, lead, magnesium, or aluminum. Such carriers are disclosed in U.S. Pat. Nos. 4,042,518; 4,478,925; and 4,546,060.

Carrier particles can be uncoated or can be coated with a thin layer of a film-forming resin to establish the correct triboelectric relationship and charge level with the toner employed. Examples of suitable resins are the polymers described in U.S. Pat. Nos. 3,547,822; 3,632,512; 3,795,618 and 3,898,170 and Belgian Patent No. 797,132. Other useful resins are fluorocarbons such as polytetrafluoroethylene, poly(vinylidene fluoride), mixtures of these, and copolymers of vinylidene fluoride and tetrafluoroethylene. See for example, U.S. Pat. Nos. 4,545,060; 4,478,925; 4,076,857; and 3,970,571. Polymeric fluorocarbon coatings can aid the developer to meet the electrostatic force requirements mentioned above by shifting the carrier particles to a position in the triboelectric series different from that of the uncoated carrier core material to adjust the degree of triboelectric charging of both the carrier and toner particles. The polymeric fluorocarbon coatings can also reduce the frictional characteristics of the carrier particles in order to improve developer flow properties; reduce the surface hardness of the carrier particles to reduce carrier particle breakage and abrasion on the photoconductor and other components; reduce the tendency of toner particles or other materials to undesirably permanently adhere to carrier particles; and alter electrical resistance of the carrier particles.

In a preferred embodiment of the invention, the carrier is strontium ferrite coated with poly(methyl methacrylate) (PMMA) on a 2 percent weight/weight basis or strontium ferrite coated with dehydrofluorinated and oxidized fluorocarbon as disclosed in U.S. Pat. No. 4,726,994, the specification of which is hereby incorporated by reference herein. The fluorocarbon is coated on a 0.5 percent weight/weight basis. The fluorocarbon carrier is also referred to herein as "modified Kynar®." The currently preferred carrier is treated with a basic solution of hydrogen peroxide.

In a particular embodiment, the developer of the invention contains from about 1 to about 20 percent by weight of toner of the invention and from about 80 to about 99 percent by weight of carrier particles. Usually, carrier particles are larger than toner particles. Conventional carrier particles have a particle size of from about 5 to about 1200 micrometers and are generally from 20 to 200 micrometers.

The toners of the invention are not limited to developers which have carrier and toner, and can be used, without carrier, as single component developer.

The toner and developer of the invention can be used in a variety of ways to develop electrostatic charge patterns or latent images. Such developable charge patterns can be prepared by a number of methods and are then carried by a suitable element. The charge pattern can be carried, for example, on a light sensitive photoconductive element or a non-light-sensitive dielectric surface element, such as an insulator coated conductive sheet. One suitable development technique involves cascading developer across the electrostatic charge pattern. Another technique involves applying toner particles from a magnetic brush. This technique involves the use of magnetically attractable carrier cores. After imagewise deposition of the toner particles the image can be fixed, for example, by heating the toner to cause it to fuse to the substrate carrying the toner. If desired, the unfused image can be transferred to a receiver such as a blank sheet of copy paper and then fused to form a permanent image.

The invention is further illustrated by the following Examples. N-acylsulfonamides were prepared by the method disclosed by Kemp and Stephen, J. Chem. Soc., 1948, 11. N-sulfonylcarboximidoyl chlorides were prepared by the method disclosed by Barnikow and Richter, Z. Chem., 20(3), 97 (1980). 2-Cyanoacetamides were prepared by the method disclosed in Ried and Schleimer, Ann., 626, 98 (1959). All other chemicals were commercially available. All melting points in the Examples are uncorrected. Elemental analyses were performed by combustion techniques. Thermal stabilities (TGA) in air were determined with a Perkin-Elmer Series 7 Thermal Analysis System at a heating rate of 10° C./min from 25°–500° C. Charging and throw-off results are reported here for colorless toners. Proposed structures were confirmed by NMR.

Compound Preparation

A series of compounds were prepared and the synthesis of compound 1 is shown in detail.

Synthesis of Compound 1

A mixture of 10.41 g (50 mmol) of N,N'-di(cyanoacetyl) -1,3-propanedime and 27.98 g (100 mmol) of N-phenylsulfonylbenzene-carboximidoyl chloride in 400 mL of methylene chloride was prepared. Triethylamine (20.24 g, 200 mmol) was added dropwise over a 7 minute period with 50 mL of methylene chloride rinse. The reaction mixture was stirred for 1 hour, washed with dilute HCl and water, dried over magnesium sulfate and concentrated. The residue was treated with ligroine and then with hot ethanol. The solid was collected, recrystallized with toluene, collected and dried. The yield of the product was 14.3 g (41.2 percent of theory) and the melting point was 195.5°–197° C.

Elem. analysis for $C_{35}H_{30}N_6O_6S_2$: C, 60.51; H, 4.35; N, 12.10; S, 9.23

Found: C, 60.26; H, 4.32; N, 11.93, S, 8.81

Additional compounds were prepared in an analogous manner by appropriate selection of the starting materials. The compounds prepared are shown in Table 1 as follows:

TABLE 1

| Cpd | $R^1$ | X | Y | mp °C. | Yield | TGA °C. |
|---|---|---|---|---|---|---|
| 1 | –$(CH_2)_3$– | H | H | 195.5–197.0 | 41.2 | 283 |
| 2 | -1,3-$CH_2C_6H_4CH_2$– | H | H | amorph | 50.0 | 286 |
| 3 | -1,4-$CH_2C_6H_4CH_2$– | $CH_3$ | $CH_3$ | 256 | 4.2 | 287 |
| 4 | -1,4-$CH_2C_6H_4CH_2$– | $CH_3$ | H | 213–215 | 27.9 | 281 |
| 5 | "ODP" | $CH_3$ | H | 256–258 | 40.1 | 285 |
| 6 | "PID" | H | H | 251.5–253 | 37.6 | 290 |

"ODP" is:

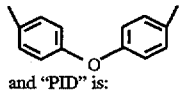

and "PID" is:

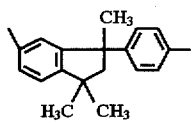

Structural formulas for the charge control agents are indicated in Table 1 above. Number designations in the Results below correspond to the number designations of structural formulas. In the Results Table, "Cpd" is the designation of the structural formula of the charge control agent; "(pph)" is the concentration of charge agent in styrene/n-butyl acrylate/divinylbenzene binder resin, expressed in parts by weight per hundred parts of binder resin; "2 min" and "10 min" are the charge to mass ratios (Q/m) in microcoulombs/gram at the indicated times, and "T.O." is throw-off in milligrams. The throw off test is described in more detail below.

Preparation of Colorless Toners

A dry blend of 50.0 grams of poly(styrene-co-n-butyl acrylate-co-divinylbenzene) and 0.5 gram of the sulfonamide charge control agent (compound 1) was added to a heated two-roll compounding mill. The roller surfaces were set to 150° C. The melt was exercised on the mill for 20 minutes, then was removed and cooled. The resulting slab was first coarse ground to 2 mm size on a laboratory mill, then finely pulverized to approximately 12 micrometer size on a Trost TX jet mill. The toner thus prepared had a concentration of charge control agent of 1 part per hundred parts of styrene/n-butyl acrylate/divinylbenzene binder resin. This procedure was repeated, varying the concentration of charge control agent to provide concentrations of 2 and 4 parts per hundred (pph), on the same basis.

Preparation of Developers-PMMA Coated Carrier

Developer was prepared for each of the toners indicated above, by mixing toner particles prepared as described above at a weight concentration of 12% toner with carrier particles comprising strontium ferrite cores thinly coated (approximately 2 percent by weight) with poly(methyl methacrylate). The volume average particle size of the carrier particles was from about 25 to 35 micrometers.

Preparation of Developers-Modified Kylar® Coated Carrier

Developer was prepared for each of the toners indicated above, by mixing toner particles prepared as described above at a weight concentration of 12% toner with carrier particles comprising strontium ferrite cores thinly coated (approximately 0.5 percent weight/-weight) with dehydrofluorinated and oxidized fluorocarbon as disclosed in U.S. Pat. No. 4,726,994. The carrier was treated with basic hydrogen peroxide. The volume average particle size of the carrier particles was from about 25 to 35 micrometers.

Evaluation of Toner Charging

Toner charge was then measured in microcoulombs per gram of toner (µc/g) in a "MECCA" device. Prior to measuring the toner charge, the developer was vigorously shaken or "exercised" to cause triboelectric charging by placing a 4 gram sample of the developer into a plastic vial, capping the vial and shaking the vial on a "wrist-action" robot shaker operated at about 2 Hertz and an overall amplitude of about 11 cm for 2 minutes. Toner charge level after shaking was measured for each sample by placing a 100 milligram sample of the charged developer in a MECCA apparatus and measuring the charge and mass of transferred toner in the MECCA apparatus. This involves placing the 100 milligram sample of the charged developer in a sample dish situated between electrode plates and subjecting it, simultaneously, for 30 seconds, to a 60 Hz magnetic field and an electric field of about 2000 volts/cm between the plates. The toner is released from the carrier and is attracted to and collects on the plate having polarity opposite to the toner charge. The total toner charge is measured by an electrometer connected to the plate, and that value is divided by the weight of the toner on the plate to yield the charge per mass of toner (Q/m). The toner charge level (i.e. charge-to-mass ratio) was also taken after exercising the developer for an additional 10 minutes by placing the magnetized developer in a glass bottle on top of a cylindrical roll with a rotating magnetic core rotating at 2000 revolutions per minute. The magnetic core had 12 magnetic poles arranged around its periphery, in an alternating north and south fashion. This closely approximates typical actual usage of the developer in an electrostatographic development process. After this additional 10 minute exercising, the toner charge was measured in a MECCA apparatus. Values are reported in the Results Table as Q/m at 2 min. and 10 min.

Evaluation of Throw-Off

Throw-off values (T.O.) were determined by taking the 4 gram developer sample at 12% toner concentration that had been exercised for 10 minutes (following the 2 minute exercising), admixing in 6% more toner to provide a final toner concentration of about 18%), followed by 2 minutes more exercise on the wrist action shaker. This developer was then placed on a roll containing a rotating magnetic core, similar to a magnetic brush roll used for electrostatic development. A plexiglass housing contained the assembly, and had a vacuum filter funnel mounted directly over the roll. The weight of toner, in milligrams, collected on a piece of filter paper after one minute of running the magnetic core at 2000 revolutions per minute was reported as the throw-off value.

Results

| Cpd. | pph | PMMA Carrier | | | Modified Kynar ® Carrier | | |
|---|---|---|---|---|---|---|---|
| | | 2 min | 10 min | T.O. | 2 min | 10 min | T.O. |
| 1 | 1 | −19.3 | −33.4 | 9.8 | −6.6 | −46.8 | 0.6 |
| 1 | 2 | −23.7 | −32.1 | 7.1 | −9.0 | −27.8 | 2.8 |
| 1 | 4 | −27.2 | −27.2 | 6.6 | −13.8 | −13.2 | 3.5 |
| 2 | 1 | −17.1 | −33.6 | 3.5 | −10.1 | −52.1 | 0.2 |
| 2 | 2 | −19.1 | −29.6 | 7.8 | −12.0 | −40.3 | 0.2 |
| 2 | 4 | −24.9 | −26.8 | 6.2 | −18.6 | −24.4 | 1.1 |
| 4 | 1 | −18.2 | −32.1 | 13.2 | −8.8 | −50.0 | 0.5 |
| 4 | 2 | −20.0 | −21.9 | 1.3 | −11.0 | −25.9 | 0.8 |
| 4 | 4 | −25.7 | −20.2 | 1.7 | −17.0 | −12.6 | 13.4 |
| 5 | 1 | −23.13 | −29.39 | 8.5 | −18.5 | −48.8 | 0.3 |
| 5 | 2 | −30.38 | −29.68 | 7.0 | −25.9 | −29.2 | 0.9 |
| 5 | 4 | −31.75 | −23.14 | 3.3 | −26.7 | −12.5 | 1.8 |
| 6 | 1 | −25.86 | −53.45 | 5.4 | −27.5 | −59.3 | 0.9 |
| 6 | 2 | −34.67 | −55.61 | 4.3 | −36.5 | −46.6 | 1.2 |
| 6 | 4 | −38.70 | −48.69 | 3.8 | −44.1 | −24.3 | 1.4 |

While specific embodiments of the invention have been shown and described herein for purposes of illustration, the protection afforded by any patent which may issue upon this application is not strictly limited to a disclosed embodiment; but rather extends to modifications and arrangements which fall fairly within the scope of the claims which are appended hereto.

We claim:

1. A toner composition comprising a polymeric binder and a charge control agent having the general structure:

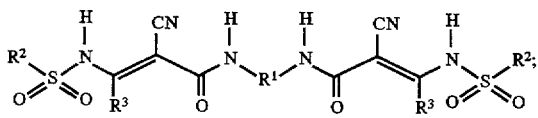

wherein $R^1$ represents alkylene; arylene; arylenedialkylene; alkylenediarylene; oxydialkylene; or oxydiarylene;

$R^2$ represents alkyl containing from 1 to 20 carbons; cycloalkyl containing from 3 to 18 carbons; unsubstituted aromatic ring systems; aromatic ring systems substituted with alkyl, hydroxy, alkoxy, carboxy, carboalkoxy, nitro, halo, cyano, amino, dialkylamino, acyl, trihalomethyl or alkylsulfonyl; or heteroaromatic ring systems having (a) a solitary ring or 2 to 3 linked or fused rings and (b) containing from 3 to 34 carbons;

$R^3$ represents alkyl containing from 1 to 20 carbons; cycloalkyl containing from 3 to 18 carbons; unsubstituted aromatic ring systems; aromatic ring systems substituted with alkyl, hydroxy, alkoxy, carboxy, carboalkoxy, nitro, halo, cyano, amino, dialkylamino, acyl, trihalomethyl or alkylsulfonyl; heteroaromatic ring systems having (a) a solitary ring or 2 to 3 linked or fused rings and (b) containing from 3 to 34 carbons; unsubstituted ethenyl; or ethenyl substituted with alkyl containing from 1 to 20 carbons; aryl containing from 5 to 10 carbons; or aryl substituted with alkyl, hydroxy, carboxy, carboalkoxy, nitro, halo, cyano, amino, dialkylamino, acyl, trihalomethyl, or alkylsulfonyl.

2. The toner composition according to claim 1 wherein said charge control agent has the general structure:

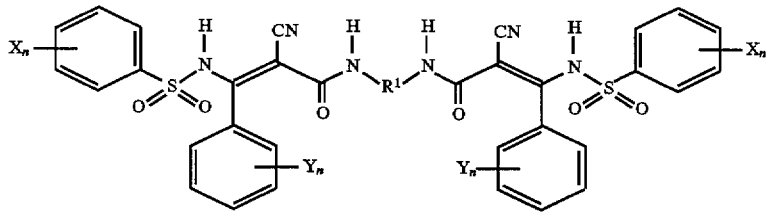

wherein X and Y, each of which can be the same or different, are hydrogen, alkyl, hydroxy, alkoxy, carboxy, carboalkoxy, halo, nitro, cyano, amino, dialkylamino, acyl, trihalomethyl or alkylsulfonyl and $R^1$ is as defined above; and each n is independently an integer of from 0 to 5.

3. A toner composition according to claim 1 wherein said polymeric binder is a styrenic/acrylic copolymer having a glass transition temperature in the range of about 500° C. to about 100° C.

4. A toner composition according to claim 3 wherein said polymeric binder is a copolymer of styrene and n-butyl acrylate, crosslinked with divinylbenzene.

5. The toner composition according to claim 4 wherein the weight ratio of styrene to n-butyl acrylate is in the range of from 90:10 to 60:40 and the divinylbenzene is used at a level of 3.0 weight percent or less.

6. The toner composition according to claim 1 wherein the weight percent of charge control agent is in the range of about 0.5 to 7.0 weight percent.

7. The toner composition according to claim 1 further comprising a colorant.

8. An electrostatographic developer comprising a carrier and a toner composition; wherein the toner compositions contains a polymeric binder and a charge control agent having the general structure:

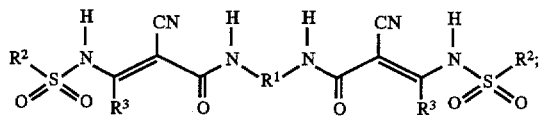

wherein $R^1$ represents alkylene; arylene; arylenedialkylene; alkylenediarylene; oxydialkylene; or oxydiarylene;

$R^2$ represents alkyl containing from 1 to 20 carbons; cycloalkyl containing from 3 to 18 carbons; unsubstituted aromatic ring systems; aromatic ring systems substituted with alkyl, hydroxy, alkoxy, carboxy, carboalkoxy, nitro, halo, cyano, amino, dialkylamino, acyl, trihalomethyl or alkylsulfonyl; or heteroaromatic ring systems having (a) a solitary ring or 2 to 3 linked or fused rings and (b) containing from 3 to 34 carbons;

$R^3$ represents alkyl containing from 1 to 20 carbons; cycloalkyl containing from 3 to 18 carbons; unsubstituted aromatic ring systems; aromatic ring systems substituted with alkyl, hydroxy, alkoxy, carboxy, carboalkoxy, nitro, halo, cyano, amino, dialkylamino, acyl, trihalomethyl or alkylsulfonyl; heteroaromatic ring systems having (a) a solitary ring or 2 to 3 linked or fused rings and (b) containing from 3 to 34 carbons; unsubstituted ethenyl; or ethenyl substituted with alkyl containing from 1 to 20 carbons; aryl containing from 5 to 10 carbons; or aryl substituted with alkyl, hydroxy, carboxy, carboalkoxy, nitro, halo, cyano, amino, dialkylamino, acyl, trihalomethyl, or alkylsulfonyl.

9. A developer according to claim 8 wherein said carrier is strontium ferrite coated with poly(methylmethacrylate) on a 2 percent weight/weight basis.

10. A developer according to claim 8 wherein said carrier is strontium ferrite coated with dehydrofluorinated and oxidized fluorocarbon.

\* \* \* \* \*